(12) United States Patent
Ehrmaier et al.

(10) Patent No.: US 10,647,628 B2
(45) Date of Patent: May 12, 2020

(54) SELECTIVE OLIGOMERIZATION OF OLEFINS

(71) Applicant: Evonik Degussa GmbH, Essen (DE)

(72) Inventors: Andreas Ehrmaier, Moosburg (DE); Ricardo Bermejo De Val, München (DE); Maria Cruz Sanchez-Sanchez, München (DE); Yue Liu, Unterhaching (DE); Johannes A. Lercher, Ottobrunn (DE); Stephan Peitz, Oer-Erkenschwick (DE); Guido Stochniol, Haltern am See (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/905,093

(22) Filed: Feb. 26, 2018

(65) Prior Publication Data

US 2018/0251410 A1  Sep. 6, 2018

(30) Foreign Application Priority Data

Feb. 27, 2017 (EP) .................................... 17158066

(51) Int. Cl.
| | | |
|---|---|---|
| *C07C 2/12* | (2006.01) | |
| *B01J 29/76* | (2006.01) | |
| *C07C 11/08* | (2006.01) | |
| *C01B 39/14* | (2006.01) | |

(52) U.S. Cl.
CPC .............. *C07C 2/12* (2013.01); *B01J 29/7607* (2013.01); *C07C 11/08* (2013.01); *C01B 39/14* (2013.01); *C07C 2529/76* (2013.01)

(58) Field of Classification Search
CPC . C07C 2/00–36; C07C 11/08; C07C 2529/76; C07C 2/12; B01J 29/7607; B01J 37/30; B01J 29/7207; B01J 2229/18; C01B 39/14
See application file for complete search history.

(56) References Cited

U.S. PATENT DOCUMENTS

| | | |
|---|---|---|
| 6,846,965 B1 | 1/2005 | Schulz et al. |
| 6,852,898 B2 | 2/2005 | Schulz et al. |
| 7,291,759 B2 | 11/2007 | Heidemann et al. |
| 9,200,216 B2 | 12/2015 | Boeing et al. |
| 9,682,898 B2 | 6/2017 | Peitz et al. |
| 2004/0181105 A1 | 9/2004 | Heidemann et al. |
| 2011/0306812 A1* | 12/2011 | Rohde ........................ C07C 2/12 585/326 |
| 2013/0131416 A1 | 5/2013 | Crone et al. |
| 2015/0336861 A1 | 11/2015 | Geilen et al. |
| 2015/0367336 A1* | 12/2015 | Trukhan ................. B01J 29/763 423/239.2 |
| 2016/0263562 A1* | 9/2016 | Boal ...................... B01J 29/047 |

FOREIGN PATENT DOCUMENTS

WO  9925668  5/1999

OTHER PUBLICATIONS

European Patent Office Search Report for Application No. 18158148.9 dated Jun. 29, 2018, 2 pages.
Deimund et al., "Nickel-Exchanged Zincosilicate Catalysts for the Oligomerization of Propylene," ACS Catal., 2014, 4(11), 4189-4195.
Klier et al., "Spectra of zynthetic zeolites containing transition metal ions—II. Ni2+ ions in type a linde molecular sieves," Journal of Physics and Chemistry of Solids, 1968, 29(6), 951-957.
Nkosi et al., "The oligomerization of butenes with partially alkali exchanged NiNaY zeolite catalysts," Applied Catalysis A: General, 1997, 158(1-2), 225-241.
Tungler et al., "Magnetic Study of Zeolite-Supported Nickel Catalysts," Acad. Phys. Chem., 1978, 24(1-2), 319-325.
International Search Report dated Aug. 26, 2014 in PCT/EP2014/063374.

* cited by examiner

*Primary Examiner* — Ali Z Fadhel
(74) *Attorney, Agent, or Firm* — Michael Best & Friedrich LLP

(57) ABSTRACT

The invention relates to a catalyst system for oligomerizing olefins over a catalyst comprising nickel, to the use of this catalyst and to a method for dimerizing olefins.

13 Claims, No Drawings

SELECTIVE OLIGOMERIZATION OF OLEFINS

CROSS-REFERENCE TO RELATED APPLICATION

This patent application claims the benefit of priority to European Application No. 17158066.5, filed on Feb. 27, 2017, the disclosure of which is incorporated by reference herein in its entirety, and priority to which is hereby claimed.

The invention relates to a catalyst system for oligomerizing olefins over a catalyst comprising nickel, to the use of this catalyst and to a method for oligomerizing olefins.

In general, oligomerization is understood to mean the reaction of hydrocarbons with themselves to form correspondingly longer-chain hydrocarbons, the so-called oligomers. Olefins having from two to eight carbon atoms can be oligomerized quite efficiently. Thus, for example, an olefin having six carbon atoms (hexene) can be formed by oligomerization of two olefins having three carbon atoms. The oligomerization of two molecules with each other is also referred to as dimerization.

The resulting oligomers, particularly the dimers of $C_3$-$C_5$-olefins, are intermediates which can be used, for example, for preparing aldehydes, carboxylic acids and alcohols.

If n-butenes—which are linear olefins having four carbon atoms—are subjected to an oligomerization, essentially olefins having eight carbon atoms (more precisely: dibutene) and also olefins having twelve carbon atoms (C12-olefins, "tributene") and to a lesser extent olefins having more than twelve carbon atoms (C12+-olefins) are formed. The $C_8$-olefins, which are formed from linear butenes, may be converted to the corresponding nonanols by hydroformylation and subsequent hydrogenation, which are used in turn for preparing predominantly plasticizers.

The oligomerization of olefins is carried out industrially either in a homogeneous phase over a catalyst in solution, or heterogeneously over a solid catalyst, or with a biphasic catalyst system.

In the case of the heterogeneously catalyzed processes, oligomerization over acidic catalyst is long-established. For example, zeolites or phosphoric acid on supports are used industrially. In this case, isomeric mixtures of branched olefins are obtained. One example of the acidic catalysis of oligomerizations of olefins is found in WO 92/13818.

For the non-acidic, heterogeneously catalyzed oligomerization of olefins, with high dimer selectivity, nickel compounds on support materials are frequently employed in the art. One catalyst of this kind is a fixed-bed nickel catalyst which is used in the OCTOL process of Evonik Industries AG (Hydrocarbon Process., Int. Ed. (1988) 65 (2, Sect. 1, 31-33). Supported nickel catalysts for this purpose are known. For instance, WO 95/14647 describes a nickel catalyst with a support material consisting of the components titanium oxide and/or zirconium oxide, silicon oxide and optionally aluminium oxide and some alkali metal oxide, for the olefin oligomerization. Mixtures of linear butenes are oligomerized over these catalysts to $C_8$-olefins with a selectivity of below 75%.

The use of zeolites as support material has proven to be disadvantageous since these usually have relatively large pores and a high proportion of protons. The latter result in acid-catalyzed secondary reactions, in particular the formation of branched products.

The object of the present invention is to provide an improved catalyst system which can overcome the disadvantages mentioned above and in particular can lead to an improved conversion-dependent selectively for linear dimers when used as catalyst in the oligomerization.

It has been found, surprisingly, that the catalyst system according to the invention fulfils the objective.

Accordingly, a first subject matter of the present invention is a method for oligomerizing olefins, wherein the olefins are present in gaseous or supercritical form and wherein a Ni ion-exchanged zeolite of Linde Type A is used as catalyst.

It has been shown, surprisingly, that a high yield of linear dimers can be obtained by using the specific Ni ion-exchanged small-pore zeolites of Linde Type A. This is surprising insofar as the formation of a high proportion of branched products occurs due to acid catalysis as a typical secondary reaction, especially in zeolites.

The catalyst used in the context of the present invention is a Ni ion-exchanged zeolite of the Linde Type A (abbreviation LTA). Zeolites of the Linde Type A are often also referred to as zeolite A for short. They are based on the chemical formula $|Na+_{12} (H_2O)_{27}|_8[Al_{12}Si_{12}O_{48}]_8$ and have a cubic unit cell with a comparatively small pore opening (8-MR). A precise description of this zeolite type is available from the "International Zeolite Association" (www.iza-on-line.org). The synthesis of zeolites of Linde Type A is described in H. Robson, K. P. Lillerud, Verified Synthesis of zeolitic materials, Second revised Edition, 2001, Elsevier, page 179 ff. An LTA is preferably used in its potassium, sodium or calcium form, especially in its sodium or calcium form. Such zeolites are commercially available, for example from Sigma Aldrich.

There are various methods for ion exchange of zeolites. In this case, the original cations of potassium, sodium or calcium incorporated in the zeolite are exchanged for the desired cations, for example nickel. This is easily possible since the cations in the zeolite are bonded to the anionic skeleton only via an ionic interaction. Ion exchange with nickel may be carried out, for example, by means of liquid ion exchange from a corresponding nickel salt-containing solution.

In the context of the present invention, ion exchange is carried out particularly preferably by liquid ion exchange.

In the simplest embodiment of the present invention, the sodium- or calcium-based LTA is mixed with a nickel salt-containing solution. The nickel salt-containing solution is preferably an aqueous solution of nickel salts, especially the corresponding nitrate, halide, sulfate, acetate, citrate, carbonate, the nitrate being particularly preferred.

The concentration of the nickel salt in the nickel salt-containing solution is in the range of 0.001 mol/l to 2.5 mol/l, particularly 0.005 mol/l to 0.5 mol/l, wherein 0.01 mol/l to 0.1 mol/l is especially preferred.

The liquid ion exchange with nickel is generally carried out over a period of 2 to 48 hours, preferably 12 to 36 hours, 20 to 28 hours being especially preferred. In this case it is advantageous to carry out the liquid ion exchange at a temperature of 60 to 100° C., preferably at 80° C.

Subsequently, the catalyst can be processed by methods known to those skilled in the art. The catalyst is preferably washed after the liquid ion exchange, preferably with water. Subsequent calcination of the catalyst is recommended, in particular at temperatures of 400 to 600° C., preferably at temperatures around 500° C. The calcination can be conducted in this case preferably in the presence of air.

The proportion of nickel in the catalyst according to the invention is between 1 and 10 wt %, preferably 2 to 8 wt % and especially preferably between 4 and 7 wt %. The nickel in this case is not present in its metallic form but as $Ni^{2+}$ in oxidic form, which need not necessarily be present stoichiometrically ($NiO_x$ where $x \leq 1$).

In a further embodiment of the present invention, the cations of potassium, sodium or calcium incorporated in the zeolite can additionally be at least partially exchanged with other alkali metal and/or alkaline earth metal ions. The aforementioned alkali metal and/or alkaline earth metal ions are particularly preferably lithium and/or magnesium.

In the context of the present invention, it has been found, surprisingly, that the conversion increases and/or the isomer structure of the dimers is improved by the additional exchange with lithium and/or magnesium ions, as a result of which the overall process can be operated more cost-effectively.

The exchange with alkali metal and/or alkaline earth metal ions is preferably carried out before the liquid ion exchange with nickel. In the simplest embodiment of the present invention, the exchange with alkali metal and/or alkaline earth metal ions is also carried out by liquid ion exchange. For this purpose, the LTA used is mixed with solutions of the appropriate alkali metal and/or alkaline earth metal salts. These preferably take the form of aqueous solutions of the appropriate alkali metal and/or alkaline earth metal salts, wherein the corresponding nitrates, halides, sulfates, acetates, citrates, carbonates may be used, wherein solutions of the corresponding alkali metal and/or alkaline earth metal halides are particularly preferred. Very particular preference is given to using lithium chloride and magnesium chloride.

Also in the case of this liquid ion exchange with alkali metal and/or alkaline earth metal ions, the zeolite may also be processed by methods known to those skilled in the art. The zeolite is preferably washed after the liquid ion exchange, also preferably with water. Subsequent calcination of the catalyst is also recommended here, in particular at temperatures of 400 to 600° C., preferably at 500° C. The calcination can be conducted in this case preferably in the presence of air.

The proportion of alkali metal and/or alkaline earth metal ions introduced by means of liquid ion exchange into the catalyst according to the invention is between 0.02 and 8.8 wt %, preferably between 0.1 and 3 wt % and especially preferably between 0.2 and 1.5 wt %.

In the method according to the invention, the reactant streams used may be streams which compromise C2- to C10-, preferably C2- to C6-olefins or mixtures thereof. Suitable reactant streams may compromise, among others, α-olefins, internal olefins (for example 2-olefins or 3-olefins) and cycloalkenes or mixtures thereof. In a particularly preferred embodiment, the reactant streams comprise a mixture of butenes which can comprise n-butane and/or isobutane, and small amounts of other C4-hydrocarbons.

A reactant stream preferably comprises few further unsaturated compounds and practically no polyunsaturated compounds such as dienes or acetylene derivatives, preferably less than 100 ppm by weight in relation to the olefins in the reactant stream. Further preference is given to using olefin mixtures comprising less than 5% by mass, in particular less than 2% by mass of branched olefins, based on the olefin content.

Propylene is produced industrially by cleavage of naphtha and is a commodity chemical which is readily available. C5-olefins are present in light petroleum fractions from refineries or crackers. Technical mixtures which comprise linear C4 olefins are light petroleum fractions from refineries, C4 fractions from FC crackers or steam crackers, mixtures from Fischer-Tropsch syntheses, mixtures from the dehydrogenation of butanes, and mixtures formed by metathesis or from other industrial processes. For the method according to the invention, for example, suitable mixtures of linear butenes are obtainable from the $C_4$ fraction of a steam cracker. In this case, butadiene is removed in the first step. This is accomplished either by extraction or extractive distillation of the butadiene or selective hydrogenation thereof. In both cases, a practically butadiene-free $C_4$ fraction is obtained, raffinate I. In the second step, isobutene is removed from the $C_4$ stream, for example by production of methyl tert-butyl ether (MTBE) by reaction with methanol. Other possibilities are the reaction of the isobutene from raffinate I with water to give tert-butanol, or the acid-catalyzed oligomerization of the isobutene to give diisobutene. The now isobutene-free $C_4$ fraction, raffinate II, contains, as desired, the linear butenes and optionally butanes. Optionally, the 1-butene may be removed by distillation. Both fractions having but-1-ene or but-2-ene may be used in the method according to the invention.

In another preferred embodiment, olefin-containing material streams such as crude butane are supplied as reactant stream to the process. Further suitable reactant streams are, inter alia, raffinate I (butadiene-free C4 fraction of the steam cracker) and raffinate II (butadiene-free and isobutene-free C4 fraction of the steam cracker).

A further possibility of producing a suitable reactant stream consists of hydroisomerizing raffinate I, raffinate II or a similarly constituted hydrocarbon mixture in a reactive column. The products of such a procedure may include a mixture consisting of 2-butenes, small fractions of 1-butene and optionally n-butane, and also isobutane and isobutene.

The present invention further relates to a catalyst system comprising a Ni ion-exchanged zeolite of Linde Type A having a Ni content of 1 to 10 wt % (based on the total weight of catalyst).

In a particularly preferred embodiment, the catalyst according to the invention is a Ni ion-exchanged zeolite of Linde Type A having a Ni content of 1 to 10 wt %, preferably 4 to 7 wt % (based on the total weight of the catalyst) and a content of alkali metal or alkaline earth metal ions of between 0.02 and 8.8 wt %, preferably between 0.1 and 3 wt % and very particularly preferably between 0.2 and 1.5 wt %. Particular preference is given to contents in the region of 0.2 wt % for lithium and/or of 1.5 wt % for magnesium (based on the total weight of the catalyst).

The invention further relates to a method of oligomerizing n-butene, comprising the following steps
A) providing a catalyst system according to the invention,
B) oligomerizing n-butene by contacting the catalyst system with an n-butene-containing mixture.

Appropriate sources of n-butene have already been mentioned above.

In one embodiment, the proportion of dimers (also referred to as "percentage selectivity based on dimerization") based on converted reactant is at least 60%, more preferably at least 85%, particularly preferably at least 90%, especially at least 95%. In a particularly preferred embodiment, the proportion of dimers is at least 96%, more preferably at least 98%, particularly preferably at least 99%.

The oligomers produced by the method according to the invention are used, inter alia, for producing aldehydes, alcohols and carboxylic acids. For instance, the dimer of linear butenes gives a nonanal mixture by hydroformylation. This affords either the corresponding carboxylic acids by oxidation or a $C_9$-alcohol mixture by hydrogenation. The C$_9$-acid mixture may be used for producing lubricants or siccatives. The C$_9$-alcohol mixture is a precursor for the production of plasticizers, particularly dinonyl phthalates. Especially with regard to the optimal properties of the plasticizers, the highest possible linearity of the C9 alcohols and therefore also the linearity of the C8 olefins required therefor, plays a crucial role. The linearity is typically determined by the ISO index.

The linearity of the dimer fraction is described by the ISO index and represents a value for the average number of methyl branches in the dimer. For instance, n-octene contributes 0, methylheptene contributes 1 and dimethylhexene contributes 2 to the ISO index of a C8 fraction. The lower the ISO index, the more linear are the molecules which make up the respective fraction. The ISO index is calculated according to the following general formula:

$$\frac{\text{(mono-branched dimers (wt \%)} + 2 \times \text{di-branched dimers (wt \%)}}{100}$$

Accordingly, a dimer mixture having an average ISO index of 1.0 has precisely one methyl branch per dimer molecule. ISO indices around 1.0 represent the standard in Ni-containing catalyst systems. It is also known that these ISO indices are conversion-dependent, i.e. on decreasing conversion per pass (i.e. the conversion in the straight pass through the catalyst bed) the dimer fraction is more linear. Since, due to economic considerations, the conversion cannot be selected to be arbitrarily low, a compromise always has to be made between conversion performance (space-time yield, product mass per catalyst mass and per unit time) and linearity of the products.

Catalyst systems according to the invention have now been found, when used in the oligomerization of olefins, where the product mixture obtained therefrom (dimer fraction) has an ISO index of significantly less than 1 without the conversion per pass being significantly lower than normal. Even at conversions per pass of >10%, preferably >15%, particularly preferably >20%, ISO indices of less than 0.8, preferably less than 0.7, especially preferably less than 0.65 are achieved with the catalyst systems according to the invention in the oligomerization process.

The oligomerization is generally conducted at a temperature in the range from 150 to 180° C., preferably in the range from 155 to 170° C., and at a pressure of 40 to 60 bar, preferably of 45 to 55 bar. The weight-based space velocities (reactant mass per unit catalyst mass per unit time; weight hourly space velocity (WHSV)) are in the range between 1.5 g of reactant per g of catalyst and per h (h$^{-1}$) and 1900 h$^{-1}$, preferably between 4 h$^{-1}$ and 350 h$^{-1}$, particularly preferably between 6 h$^{-1}$ and 125 h$^{-1}$.

Even without further elaboration it is believed that a person skilled in the art will be able to make the widest use of the above description. The preferred embodiments and examples are therefore to be interpreted merely as a descriptive disclosure which is by no means limiting in any way whatsoever.

The present invention is elucidated in more detail below using examples. Alternative embodiments of the present invention are obtainable analogously.

EXAMPLES

Catalyst Synthesis:

Zeolite of Linde Type A (LTA) in the sodium or calcium form (Sigma Aldrich) was pre-calcined at 500° C. for 4 h (heating rate: 5° C./min, in an air stream at 100 ml/min air) and was used either directly exchanged with nickel ions ("Ni on Na-LTA" and "Ni on Ca-LTA") or was exchanged with other co-cations prior to nickel exchange. For this exchange, the zeolite was mixed four times with a 0.5M aqueous solution of LiCl or MgCl$_2$; (20 g/g zeolite) and stirred at 80° C. for 4 h each time. After each exchange step, the liquid was removed by centrifugation and a fresh solution was added. After the last exchange step, the zeolite was washed with deionized water (2 l), dried overnight and calcined (8 hours at 500° C., heating rate: 5° C./min, in an air stream at 100 ml/min air).

For the nickel exchange, the LTA precursor was mixed with an aqueous solution of nickel nitrate at concentrations of 0.01 to 0.1 M (20 g/g catalyst) and stirred at 80° C. for 24 h. Subsequently, the catalyst precursor was washed with water (2 l), dried and calcined (8 h at 500° C., heating rate: 5° C./min, in an air stream at 100 ml/min air).

Reaction Process:

Prior to charging in the reactor, the catalyst was dried at 100° C. for at least 1 h. Then, between 10 and 200 mg of the catalyst were diluted with silicon carbide (SiC) in order to achieve a total weight of 800 mg. This mixture was installed in the middle of a 30 cm long tubular reactor having an internal diameter of 0.152 inches. SiC was used to fix the catalyst bed. The catalyst was activated in a flow of air (100 ml/min) at 450° C. for 2 h (heating rate: 10° C./min. After purging with N$_2$, the mixture was pressurized with N$_2$ and then the reactant mixture (85% 1-butene, 15% isobutane) was added via a syringe pump (ISCO SYRINGE PUMP 500 D; including cooling unit to maintain 14° C.). The desired flow rate was set (0.03-0.2 ml/min) and heating was initiated. The products which were formed in the straight pass through the catalyst bed were analyzed by online GC. Prior to GC injection, 100 ml/min H$_2$ were added in order to hydrogenate the product stream at ambient pressure by means of a Pt/Al$_2$O$_3$ catalyst.

Results:

| | | | 6 wt % Ni on Na-LTA | | | | | | |
|---|---|---|---|---|---|---|---|---|---|
| | | Space-time yield/ | C$_8$ Selectivity/% | | | | Oligomer Selectivity/% | | |
| | WHSV/ | | | Methyl | | ISO | | | |
| Conversion/% | g * g$^{-1}$ * h$^{-1}$ | g * g$^{-1}$ * h$^{-1}$ | Dimethylhexene | heptene | Octene | index | C8 | C12 | C16 |
| 12.8 | 4.3 | 0.6 | 3.0 | 46.1 | 50.8 | 0.52 | 89.5 | 10.5 | 0.0 |
| 10.5 | 6.4 | 0.7 | 0.0 | 45.5 | 54.5 | 0.46 | 100.0 | 0.0 | 0.0 |
| 6.4 | 12.8 | 0.8 | 0.0 | 40.9 | 59.1 | 0.41 | 100.0 | 0.0 | 0.0 |
| 1.9 | 25.5 | 0.5 | 0.0 | 37.0 | 63.0 | 0.37 | 100.0 | 0.0 | 0.0 |

| 6 wt % Ni on Li—Na-LTA | | | | | | | | | |
|---|---|---|---|---|---|---|---|---|---|
| Conversion/% | WHSV/h$^{-1}$ | Space-time yield/ g * g$^{-1}$ * h$^{-1}$ | Dimethylhexene | Methyl heptene | Octene | ISO index | Oligomer Selectivity/% | | |
| | | | | | | | C8 | C12 | C16 |
| 10.5 | 4.3 | 0.5 | 1.8 | 41.7 | 56.5 | 0.45 | 86.0 | 14.0 | 0.0 |
| 6.4 | 6.4 | 0.4 | 1.6 | 39.2 | 59.2 | 0.42 | 87.6 | 12.4 | 0.0 |
| 4.3 | 12.8 | 0.6 | 0.0 | 39.0 | 61.0 | 0.39 | 89.2 | 10.8 | 0.0 |

| 6 wt % Ni on Mg—Na-LTA | | | | | | | | | |
|---|---|---|---|---|---|---|---|---|---|
| Conversion/% | WHSV/h$^{-1}$ | Space-time yield/ g * g$^{-1}$ * h$^{-1}$ | Dimethylhexene | Methyl heptene | Octene | ISO index | Oligomer Selectivity/% | | |
| | | | | | | | C8 | C12 | C16 |
| 20.0 | 12.8 | 2.6 | 4.7 | 50.9 | 44.4 | 0.60 | 88.3 | 11.7 | 0.0 |
| 16.3 | 25.8 | 4.2 | 4.1 | 47.5 | 48.5 | 0.56 | 88.8 | 11.2 | 0.0 |

| 6 wt % Ni on Ca-LTA | | | | | | | | | |
|---|---|---|---|---|---|---|---|---|---|
| Conversion/% | WHSV/h$^{-1}$ | Space-time yield/ g * g$^{-1}$ * h$^{-1}$ | Dimethylhexene | Methyl heptene | Octene | ISO index | Oligomer Selectivity/% | | |
| | | | | | | | C8 | C12 | C16 |
| 34.5 | 6.4 | 2.2 | 4.9 | 54.8 | 40.2 | 0.65 | 84.0 | 16.0 | 0.0 |
| 28.6 | 12.8 | 3.7 | 4.4 | 52.0 | 43.6 | 0.61 | 85.1 | 14.9 | 0.0 |
| 24.0 | 25.5 | 6.1 | 3.3 | 47.0 | 49.7 | 0.54 | 82.9 | 15.1 | 2.0 |
| 19.0 | 38.1 | 7.2 | 2.4 | 44.2 | 53.4 | 0.49 | 87.8 | 12.2 | 0.0 |
| 12.8 | 101.5 | 13.0 | 2.4 | 37.3 | 47.1 | 0.48 | 86.6 | 13.0 | 0.4 |

| 6 wt % Ni on Li—Ca-LTA | | | | | | | | | |
|---|---|---|---|---|---|---|---|---|---|
| Conversion/% | WHSV/h$^{-1}$ | Space-time yield/ g * g$^{-1}$ * h$^{-1}$ | Dimethylhexene | Methyl heptene | Octene | ISO index | Oligomer Selectivity/% | | |
| | | | | | | | C8 | C12 | C16 |
| 37.3 | 6.4 | 2.42 | 5.5 | 53.7 | 40.8 | 0.65 | 83.9 | 16.1 | 0.0 |
| 35.2 | 12.7 | 4.8 | 4.4 | 49.9 | 45.8 | 0.59 | 83.6 | 16.4 | 0.0 |
| 32.9 | 25.6 | 8.4 | 5.1 | 50.3 | 44.6 | 0.61 | 82.2 | 15.7 | 2.2 |
| 20.4 | 102.4 | 20.9 | 3.6 | 45.4 | 51.0 | 0.53 | 88.0 | 11.1 | 0.9 |

| 6 wt % Ni on Mg—Ca-LTA | | | | | | | | | |
|---|---|---|---|---|---|---|---|---|---|
| Conversion/% | WHSV/h$^{-1}$ | Space-time yield/ g * g$^{-1}$ * h$^{-1}$ | Dimethylhexene | Methyl heptene | Octene | ISO index | Oligomer Selectivity/% | | |
| | | | | | | | C8 | C12 | C16 |
| 24.8 | 25.6 | 6.3 | 8.3 | 54.8 | 36.9 | 0.71 | 89.6 | 10.4 | 0.0 |
| 22.8 | 50.7 | 11.6 | 7.7 | 53.1 | 39.2 | 0.69 | 89.4 | 10.6 | 0.0 |

In summary, the present results show that Ni ion-exchanged zeolites of Linde Type A are highly active in butene dimerization and have high selectivity for linear and monobranched dimers. Both the activity and selectivity can be adapted by the amount and type of the co-cations. Here, this should always be based on the specific product performance (also space-time yield), i.e. an overall consideration of how much product is formed per unit space and time. High selectivities at low WHSV and/or low conversions are therefore not better from an economic point of view, since less product is formed per unit time than in a comparable reaction with lower selectivity at higher WHSV and/or higher conversion. In particular, the inventive zeolites of Linde Type A exchanged with other alkali metal or alkaline earth metal ions exhibit a particularly good combination of high selectivites (high Iso indices) at the same time with high space-time yields.

This application of a specific zeolite for highly selective olefin oligomerization is not currently known to those skilled in the art.

What is claimed is:

1. A catalyst system comprising a Ni ion-exchanged zeolite of Linde Type A having a Ni content of 1 to 10 wt % based on the total mass of the catalyst, characterized in that the cations of potassium, sodium or calcium incorporated in the zeolite are at least partially exchanged with other alkali metal or alkaline earth metal ions, wherein the proportion of alkali metal and/or alkaline earth metal ions introduced is between 0.02 and 8.8 wt %.

2. A catalyst system according to claim 1, characterized in that the Ni ion exchange is carried out by liquid ion exchange.

3. A catalyst system according to claim 2, characterized in that the alkali metal or alkaline earth metal ions are selected from lithium and/or magnesium.

4. A catalyst system according to claim 3, characterized in that the exchange with alkali metal and/or alkaline earth metal ions is carried out by liquid ion exchange.

5. A catalyst system according to claim 2, characterized in that the exchange with alkali metal and/or alkaline earth metal ions is carried out by liquid ion exchange.

6. A catalyst system according to claim 1, characterized in that the alkali metal or alkaline earth metal ions are selected from lithium and/or magnesium.

7. A catalyst system according to claim 6, characterized in that the exchange with alkali metal and/or alkaline earth metal ions is carried out by liquid ion exchange.

8. A catalyst system according to claim 1, characterized in that the exchange with alkali metal and/or alkaline earth metal ions carried out by liquid ion exchange.

9. A method for oligomerizing olefins comprising:
   oligomerizing the olefins in gaseous or supercritical form in the presence of the catalyst system of claim 1, to produce oligomers having an ISO index of less than 0.8 at a conversion per pass of >10%.

10. A method according to claim 9, characterized in that the olefins used are C2- to C6-olefins or mixtures thereof.

11. A method according to claim 9, characterized in that the olefin is n-butene.

12. A method for oligomerizing n-butene, comprising the following steps:
   A) providing a catalyst system according to claim 1,
   B) oligomerizing n-butene by contacting the catalyst system with an n-butene-containing mixture.

13. A method according to claim 12, characterized in that the oligomerization is conducted at a temperature in the range of 150 to 180° C. and a pressure of 40 to 60 bar.

* * * * *